(12) United States Patent
Vanden Hoek et al.

(10) Patent No.: US 6,579,226 B2
(45) Date of Patent: *Jun. 17, 2003

(54) DELIVERY OF CARDIAC CONSTRAINT JACKET

(75) Inventors: John C. Vanden Hoek, Elk River, MN (US); Jody L. Rivers, Mille Lac, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/921,475

(22) Filed: Aug. 3, 2001

(65) Prior Publication Data

US 2001/0047122 A1 Nov. 29, 2001

Related U.S. Application Data

(63) Continuation of application No. 09/483,567, filed on Jan. 14, 2000, now Pat. No. 6,293,906.

(51) Int. Cl.⁷ .............................. A61F 2/00; A61N 1/362
(52) U.S. Cl. ........................................... 600/37; 600/16
(58) Field of Search ............................. 600/37, 16, 114, 600/562; 128/898; 604/59

(56) References Cited

U.S. PATENT DOCUMENTS

| | | | |
|---|---|---|---|
| 3,983,863 | A | 10/1976 | Janke et al. |
| 4,048,990 | A | 9/1977 | Goetz |
| 4,403,604 | A | 9/1983 | Wilkinson et al. |
| 4,428,375 | A | 1/1984 | Ellman |
| 4,630,597 | A | 12/1986 | Kantrowitz et al. |
| 4,690,134 | A | 9/1987 | Snyders |

(List continued on next page.)

FOREIGN PATENT DOCUMENTS

| | | |
|---|---|---|
| DE | 3831540 | 4/1989 |
| DE | 3831540 C | 6/1993 |

(List continued on next page.)

OTHER PUBLICATIONS

"Abstracts From the 68th Scientific Sessions, Anaheim Convention Center, Anaheim, California, Nov. 13–16, 1995", *American Heart Association Supplement to Circulation*, vol. 92, No. 8, Abstracts 1810–1813 (Oct. 15, 1995).

(List continued on next page.)

*Primary Examiner*—Eric F. Winakur
*Assistant Examiner*—Nikita R Veniaminov
(74) *Attorney, Agent, or Firm*—Merchant & Gould P.C.

(57) ABSTRACT

A cardiac constraint jacket is formed of flexible material defining a volume between an open upper end and a lower end. The jacket is dimensioned for an apex of a patient's heart to be inserted into the volume through the open upper end and for the jacket to be slipped over the heart. A delivery device is used to place the jacket on the heart. The delivery device includes a plurality of attachment locations. Each of the attachment locations is releasably secured to separate positions surrounding a periphery of the open upper end of the jacket. The delivery device also includes a control arrangement which is selectively movable between an open position and a closed position. The control arrangement is connected to the attachment locations such that the attachment locations are in a compact array urging the open upper end of the jacket into a collapsed configuration when the control member is in the closed position. When the control arrangement is in the open position, the attachment locations are in an open array. The attachment locations urge the open upper end of the jacket into an open configuration sufficient for the heart to be inserted into the jacket volume through the open upper end and for the jacket to be slipped over said heart.

16 Claims, 11 Drawing Sheets

U.S. PATENT DOCUMENTS

| | | | |
|---|---|---|---|
| 4,821,723 | A | 4/1989 | Baker, Jr. et al. |
| 4,834,707 | A | 5/1989 | Evans |
| 4,878,890 | A | 11/1989 | Bilweis |
| 4,936,857 | A | 6/1990 | Kulik |
| 4,957,477 | A | 9/1990 | Lundback |
| 4,973,300 | A | 11/1990 | Wright |
| 4,976,730 | A | 12/1990 | Kwan-Gett |
| 5,057,117 | A | 10/1991 | Atweh |
| 5,087,243 | A | 2/1992 | Avitall |
| 5,131,905 | A | 7/1992 | Grooters |
| 5,150,706 | A | 9/1992 | Cox et al. |
| 5,186,711 | A | 2/1993 | Epstein |
| 5,192,314 | A | 3/1993 | Daskalakis |
| 5,256,132 | A | 10/1993 | Snyders |
| 5,290,217 | A | 3/1994 | Campos |
| 5,356,432 | A | 10/1994 | Rutkow et al. |
| 5,366,460 | A | 11/1994 | Eberbach |
| 5,383,840 | A | 1/1995 | Heilman et al. |
| 5,385,156 | A | 1/1995 | Oliva |
| 5,405,360 | A | 4/1995 | Tovey |
| 5,429,584 | A | 7/1995 | Chiu |
| 5,507,779 | A | 4/1996 | Altman |
| 5,524,633 | A | 6/1996 | Heaven et al. |
| 5,603,337 | A | 2/1997 | Jarvik |
| 5,647,380 | A | 7/1997 | Campbell et al. |
| 5,702,343 | A | 12/1997 | Alferness |
| 5,713,954 | A | 2/1998 | Rosenberg et al. |
| 5,800,528 | A | 9/1998 | Lederman et al. |
| 5,961,440 | A | 10/1999 | Schweich, Jr. et al. |
| 5,990,378 | A | 11/1999 | Ellis |
| 6,085,754 | A | 7/2000 | Alferness et al. |
| 6,155,968 | A | 12/2000 | Wilk |
| 6,293,906 | B1 * | 9/2001 | Vanden Hoek et al. ....... 600/37 |

FOREIGN PATENT DOCUMENTS

| | | |
|---|---|---|
| DE | 295 17 393 U1 | 3/1996 |
| EP | 0 280 564 | 8/1988 |
| GB | 2209678 | 5/1989 |
| JP | 60-203250 | 10/1985 |
| JP | 01-145066 | 6/1989 |
| SU | 1009457 | 4/1983 |
| WO | WO 96/16601 | 6/1996 |
| WO | WO 98/29041 | 7/1998 |
| WO | WO 98/58598 | 12/1998 |
| WO | WO 99/44534 | 9/1999 |

OTHER PUBLICATIONS

Capomolla et al., "Dobutamine and nitroprusside infusion in patients with severe congestive heart failure: Hemodynamic improvement by discordant effects on mitral regurgitation, left atrial function, and ventricular function", *American Heart Journal*, vol. 134, No. 6, pp. 1089–1098 (Dec. 1997).

Capouya et al., "Girdling Effect of Nonstimulated Cardiomyoplasty on Left Ventricular Function", *The Society of Thoracic Surgeons*, vol. 56, pp. 867–871 (1993).

Cohn, "The Management of Chronic Heart Failure", *The New England Journal of Medicine*, vol. 335, No. 7, pp. 490–498 (Aug. 15, 1996).

Coletta et al., "Prognostic value of left ventricular volume response during dobutamine stress echocardiography", *European Heart Journal*, vol. 18, pp. 1599–1605 (Oct. 1997).

Guasp, "Una protesis contentiva para el tratamiento de la miocardiopatia dilatada", *Revista Espanola de Cardiologia*, vol. 51, No. 7, pp. 521–528 (Jul. 1998).

Kass et al., "Reverse Remodeling From Cardiomyoplasty in Human Heart Failure", *Circulation*, vol. 91, No. 9, pp. 2314–2318 (May 1, 1995).

Levin et al., "Reversal of Chronic Ventricular Dilation in Patients With End–Stage Cardiomyopathy by Prolonged Mechanical Unloading", *Circulation*, vol. 91, No. 11, pp. 2717–2720 (Jun. 1, 1995).

Oh et al., "The Effects Of Prosthetic Cardiac Binding And Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, "Two–Bar Fabrics (Part–Set Threading)", *Warp Knitting Technology*, Columbine Press (Publishers) Ltd., Buxton, Great Britain, p. 111 (1970).

Vaynblat et al., "Cardiac Binding in Experimental Heart Failure", *Ann Thorac Surg*, vol. 64 (1997).

* cited by examiner

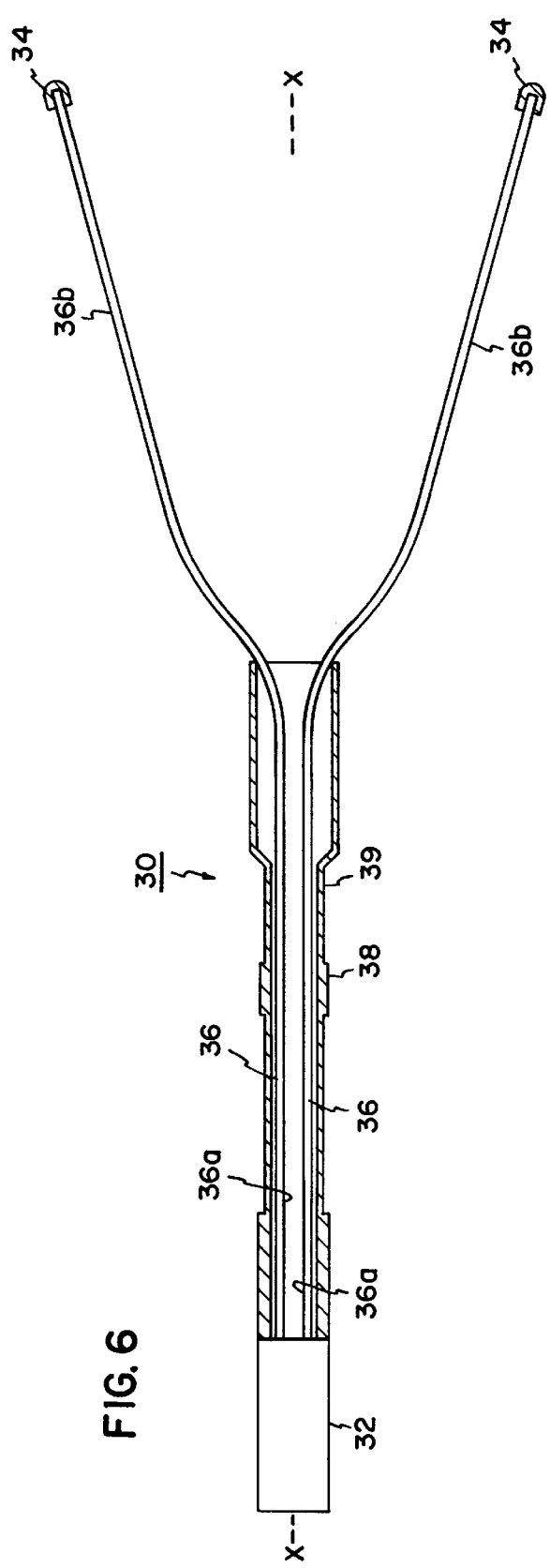
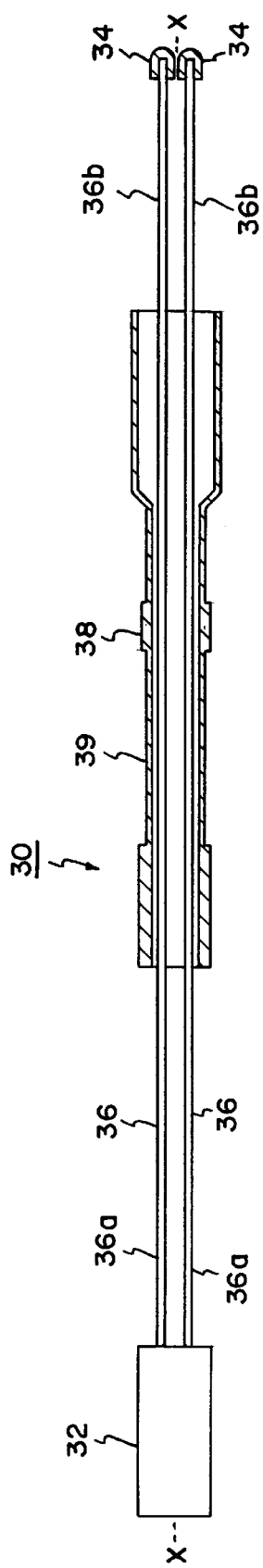
FIG. 6
FIG. 7

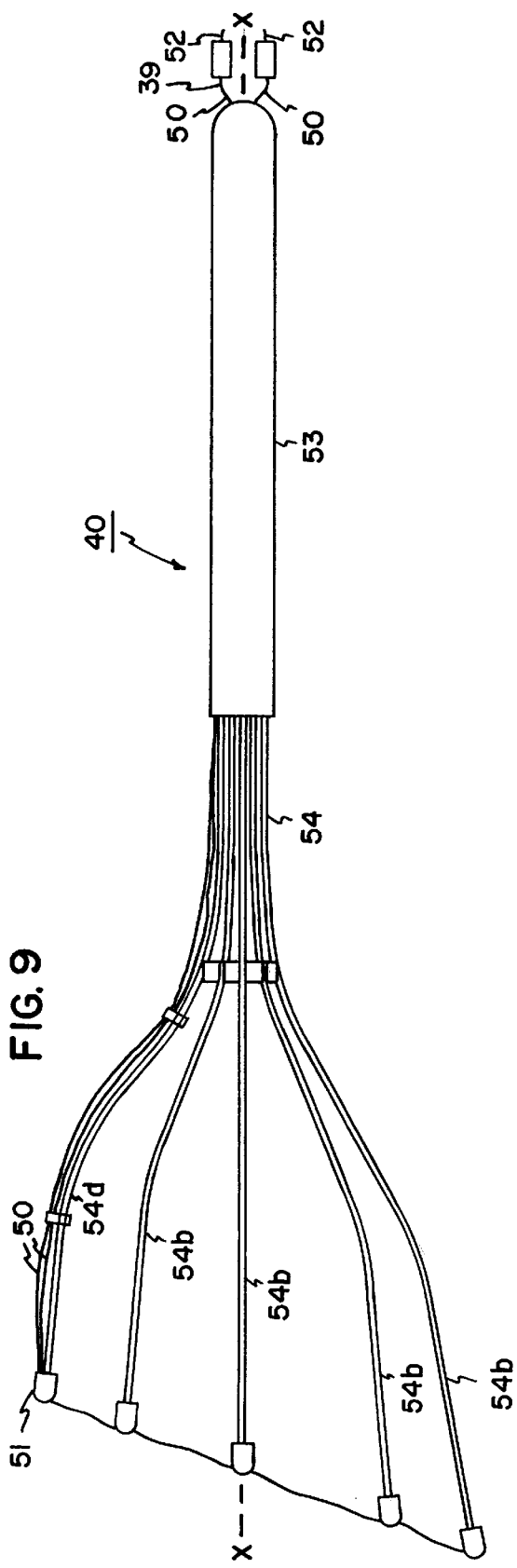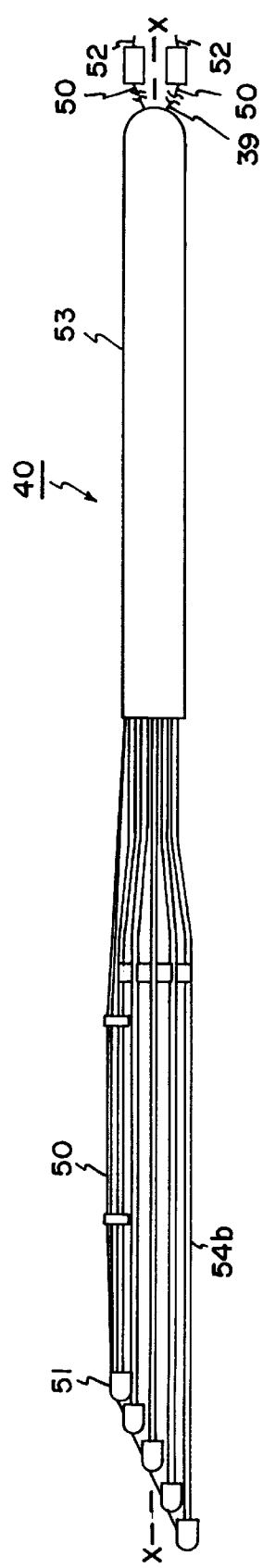

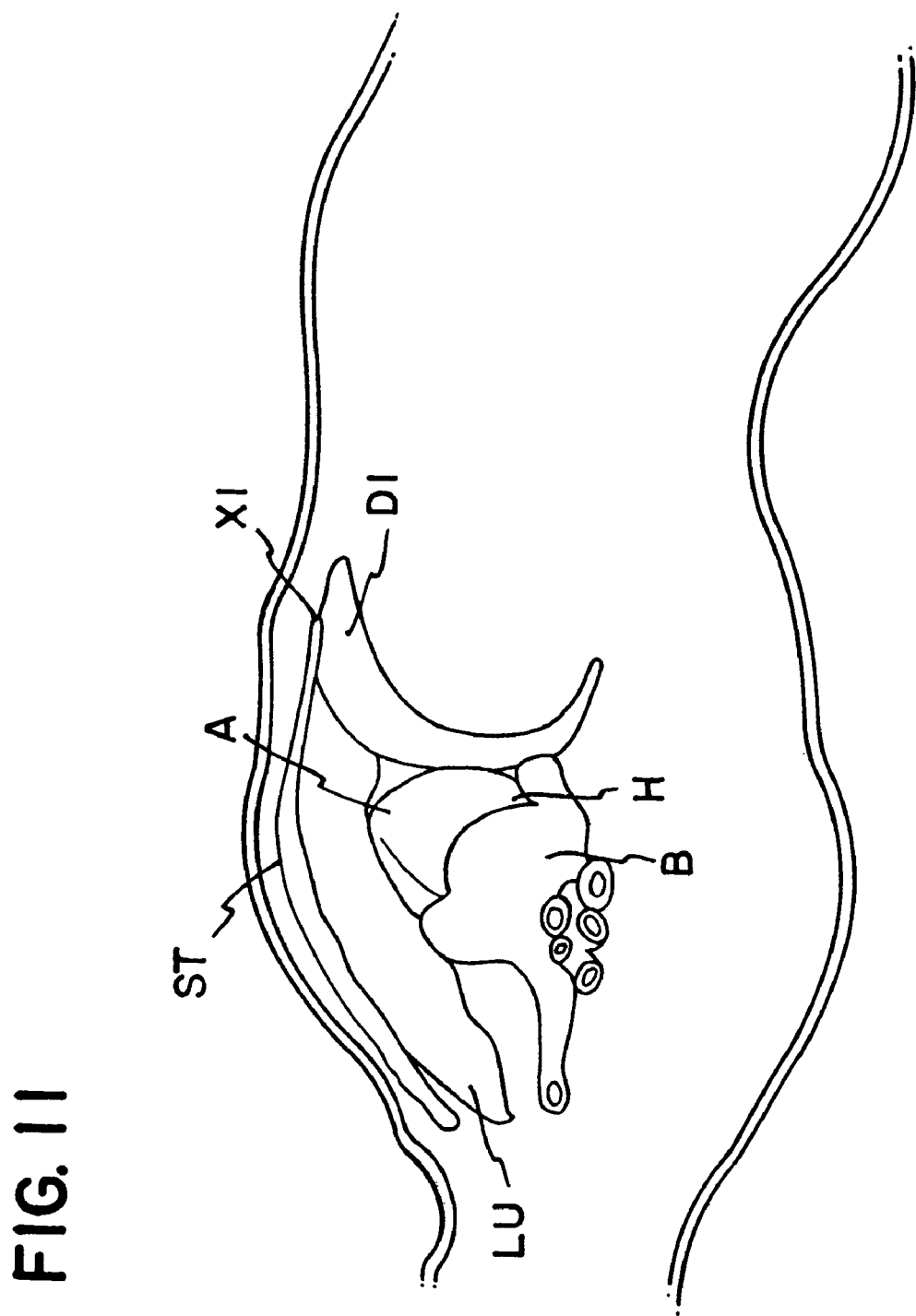

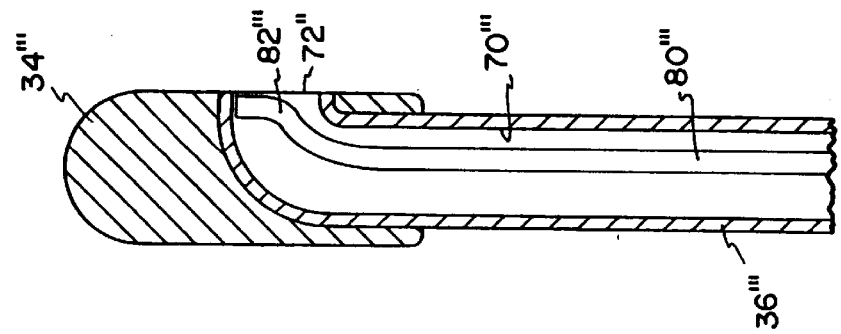
FIG. 16
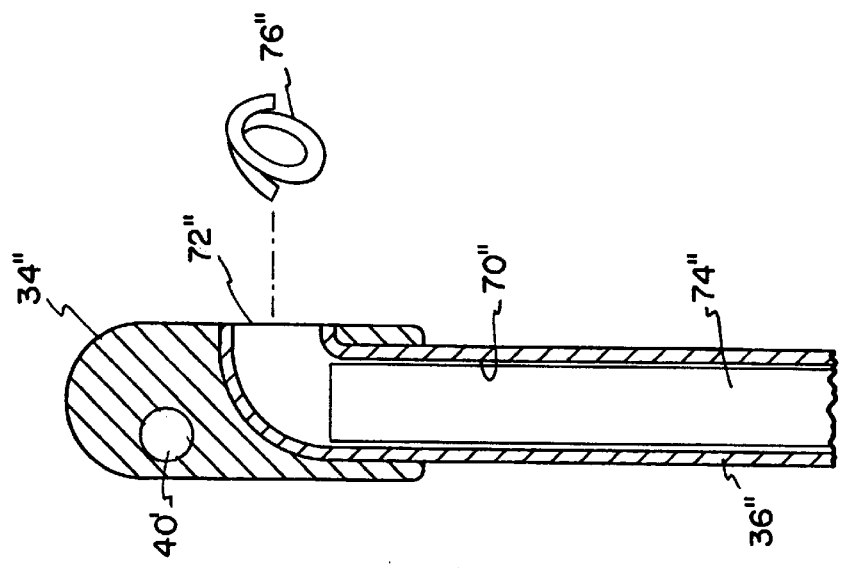
FIG. 15
FIG. 14
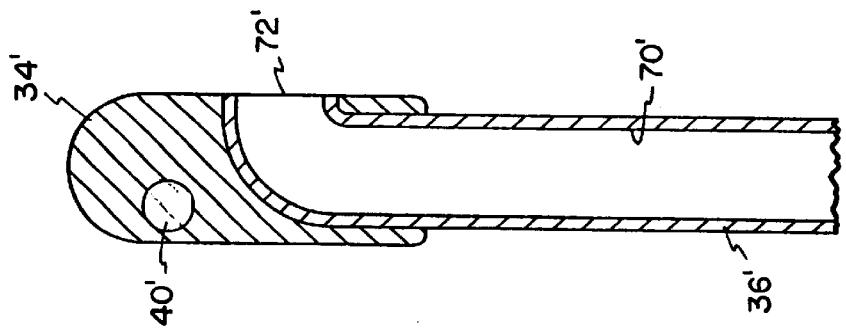
FIG. 13

DELIVERY OF CARDIAC CONSTRAINT JACKET

This application is a continuation of application Ser. No. 09/483,567, filed Jan. 14, 2000, now U.S. Pat. No. 6,293,906 which applications are incorporated herein by reference.

BACKGROUND OF THE INVENTION

1. Field of the Invention

The present invention pertains to a method and apparatus for treating congestive heart disease and related valvular dysfunction. More particularly, the present invention is directed to an apparatus and method for delivery of a cardiac constraint jacket.

2. Description of the Prior Art

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is the most commonly prescribed treatment. Drug therapy treats the symptoms of the disease and may slow the progression of the disease. Importantly, there is no cure for congestive heart disease. Even with drug therapy, the disease will progress. Further, the drugs may have adverse side effects.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one-year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8–12 months long on average and frequently a patient may have to wait about 1–2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant due to failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling From Cardiomyoplasty In Human Heart Failure: External Constraint Versus Active Assist*, 91 Circulation 2314–2318 (1995). Similarly, cardiac binding is described in Oh et al., *The Effects of Prosthetic Cardiac Binding and Adynamic Cardiomyoplasty in a Model of Dilated Cardiomyopathy*, 116 J. Thorac. Cardiovasc. Surg. 148–153 (1998), Vaynblat et al., *Cardiac Binding in Experimental Heart Failure*, 64 Ann. Thorac. Surg. 81–85 (1997) and Capouya et al., *Girdling Effect of Nonstimulated Cardiomyoplasty on Left Ventricular Function*, 56 Ann. Thorac. Surg. 867–871 (1993).

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle into the aorta. Such surgeries are expensive. The devices are at risk of mechanical failure and frequently require external power supplies. TAH devices are used as temporary measures while a patient awaits a donor heart for transplant.

Commonly assigned U.S. Pat. No. 5,702,343 to Alferness dated Dec. 30, 1997 teaches a jacket to constrain cardiac expansion during diastole. Also, PCT International Publication No. WO 98/29401 published Jul. 9, 1998 teaches a cardiac constraint in the form of surfaces on opposite sides of the heart with the surfaces joined together by a cable through the heart or by an external constraint. U.S. Pat. No. 5,800,528 dated Sep. 1, 1998 teaches a passive girdle to surround a heart. German utility model DE 295 17 393 describes a non-expansible heart pouch. PCT International Publication No. WO 98/58598 published Dec. 30, 1998 describes a cardiac pouch with an elastic limit.

A cardiac constraint device can be placed on an enlarged heart and fitted snug during diastole. For example, a knit jacket device can be loosely slipped on the heart. After such placement, the material of the jacket can be gathered to adjust the device to a desired tension. The gathered material can be sutured or otherwise fixed to maintain the tensioning. The heart may be pre-shrunk prior to placement of the device or the device may be fitted on the heart without pre-shrinking the heart. The device is adjusted to a snug fit on the heart during diastole.

When placing a cardiac constraint jacket around a heart, surgical access is made to the heart. Such access may include a full sternotomy where the sternum is split lengthwise and separated to expose the heart. Recognizing such a procedure is highly traumatic, cardiac surgery continues to explore new surgical techniques ad tools to access the heart through less invasive procedures. Also, when placing the cardiac constraint jacket on the heart, it may be necessary to manipulate the heart. Excessive manipulation is undesirable since the heart may respond by fibrillating requiring the surgeon to exercise defibrillating procedures or therapies.

The present invention is directed to improved methods and apparatus to deliver the cardiac constraint device.

SUMMARY OF THE INVENTION

According to a preferred embodiment of the present invention, a method and apparatus are disclosed for treating congestive heart disease and related cardiac complications such as valvular disorders. A cardiac constraint jacket is formed of flexible material defining a volume between an open upper end and a lower end. The jacket is dimensioned for an apex of a patient's heart to be inserted into the volume through the open upper end and for the jacket to be slipped over the heart. A delivery device is used in placing the jacket on the heart. In preferred embodiments, the delivery device includes a plurality of attachment locations. Each of the attachment locations is releasably secured at positions surrounding a periphery of the open upper end of the jacket. The delivery device also includes a control arrangement selectively movable between an open position and a closed position. The control arrangement is operatively connected to some or all of the attachment locations. The control arrangement can be selectively moved to a closed or open position. When in the closed position, the attachment locations are in a compact array position, which urges the open upper end of the jacket into a collapsed configuration. When the control arrangement is in an open position, the attachment locations are in an open array which urges the open upper end of the jacket into an open configuration sufficient for the heart to be inserted into the jacket volume through the open upper end for the jacket to be slipped over the heart.

According to the invention, the open end of the jacket may be releasably secured to the attachment locations with the control arrangement moved to the closed position. In the closed position, the delivery device and jacket can be advanced toward the apex of the heart through a restricted space. The control arrangement can then be moved to an open position when the open end of the jacket has passed through the restricted space and is in proximity to the apex for placement of the jacket on the heart.

BRIEF DESCRIPTION OF THE DRAWINGS

FIG. 6 is a longitudinal cross-sectional view of one embodiment of a delivery tool of the invention shown in an open position;

FIG. 7 is the delivery tool of FIG. 6 in a closed position;

FIG. 9 is a side view of an alternative embodiment of a delivery tool of the invention shown in an open position;

FIG. 10 is a side view of the delivery tool of FIG. 9 in a closed position;

FIG. 11 is a side view of a patient showing relative placement of internal organs to illustrate a method according to the present invention;

FIG. 13 is a side sectional view of an alternative embodiment of a spacing arm for the present invention for delivery of a bio-adhesive;

FIG. 14 is a side sectional view of a further alternative embodiment of a spacing arm for the present invention for delivery of a fastening member shown prior to delivery of the fastening member;

FIG. 15 is the view of FIG. 14 shown following delivery of the fastening member; and FIG. 16 is a side sectional view of a still further alternative embodiment of a spacing arm for the present invention for releasable attachment to a cardiac constraint jacket.

DESCRIPTION OF THE PREFERRED EMBODIMENT

A. Congestive Heart Disease

Figure 1:
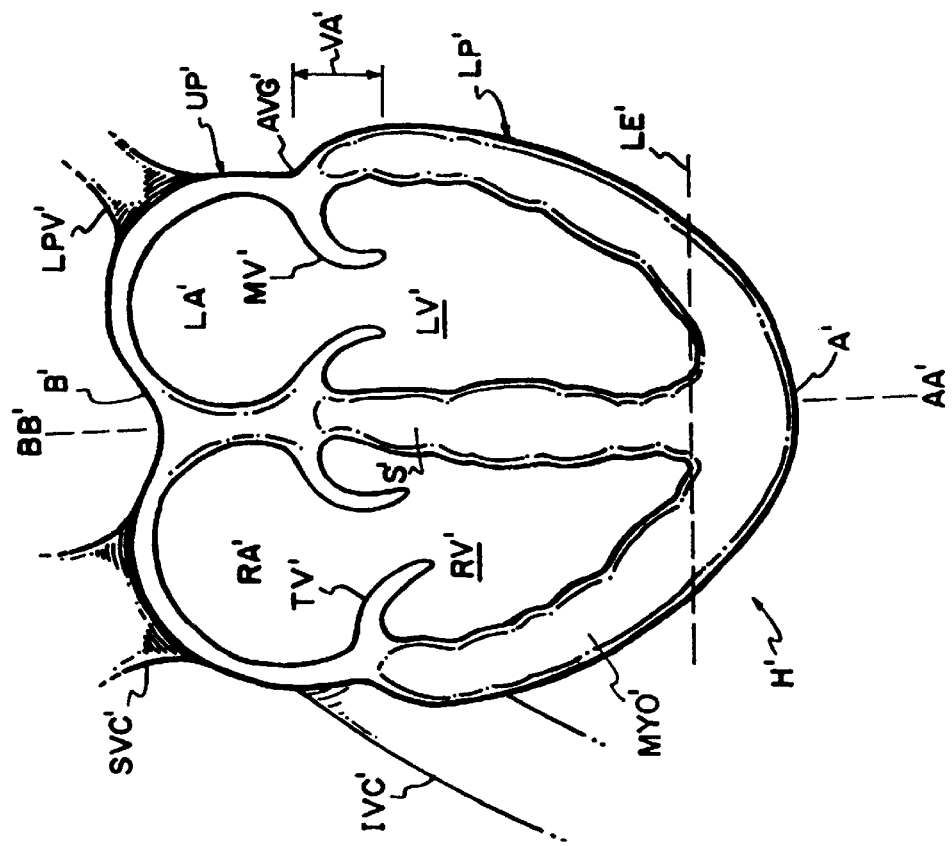
FIG. 1 is a schematic cross-sectional view of a normal, healthy human heart shown during systole.

To facilitate a better understanding of the present invention, description will first be made of a cardiac constraint device such as is more fully described in commonly assigned and copending U.S. patent application Ser. No. 09/114,757 filed Jul. 13, 1998. In the drawings, similar elements are labeled similarly throughout.

Figure 1A:
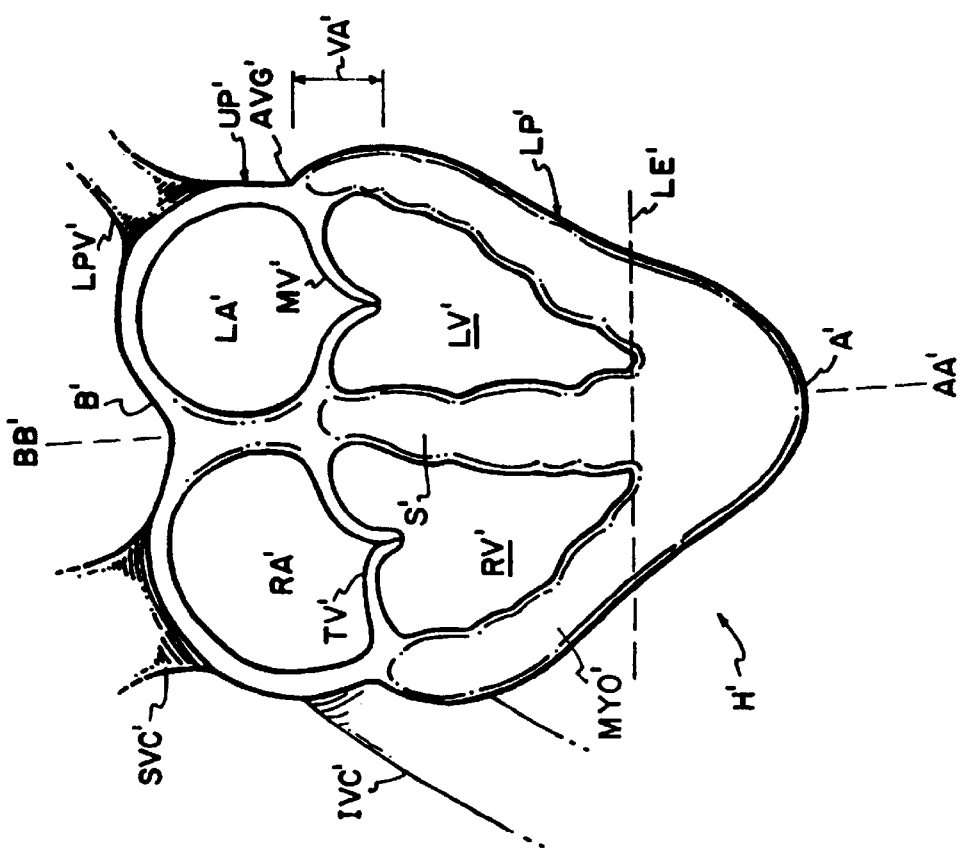
FIG. 1A is the view of FIG. 1 showing the heart during diastole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis BB'–AA' from an tipper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A–V (atrio-ventricular) groove AVG'. Extending away from the upper portion UP' are a plurality of major blood vessels communicating with the chambers RA', RV', LA', LV'. For ease of illustration, only the superior vena cava SVC', inferior vena cava IVC' and a left pulmonary vein LPV' are shown as being representative.

The heart H' contains valves to regulate blood flow between the chambers RA', RV', LA', LV' and between the chambers and the major vessels (e.g., the superior vena cava SVC', inferior vena cava IVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A–V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'–BB').

The motion of the heart H' and the variation in the shape of the heart H' during contraction and expansion is complex. The amount of motion varies considerably throughout the heart H'. The motion includes a component which is parallel to the axis AA'–BB' (conveniently referred to as longitudinal expansion or contraction). The motion also includes a component perpendicular to the axis AA'–BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2:
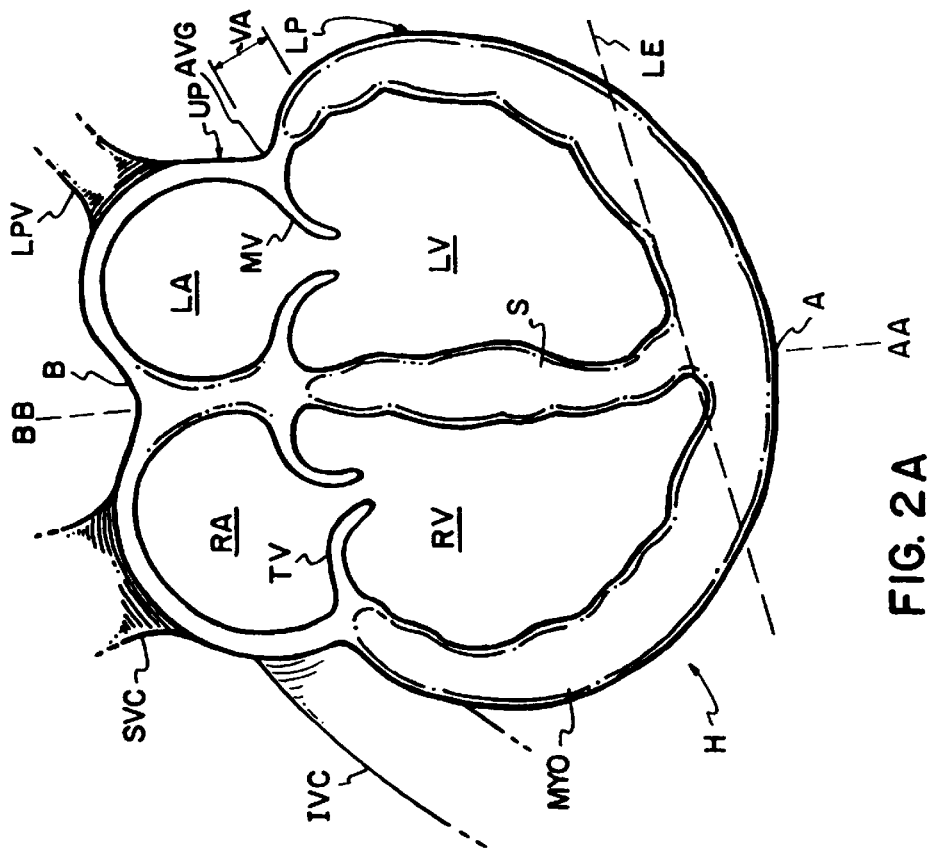
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H dilates outwardly between the apex A and the A–V groove AVG. So deformed, the diseased heart H during systole (FIG. 2) resembles the healthy heart H' during diastole (FIG. 1A). During diastole (FIG. 2A), the deformation is even more extreme.

Figure 2A:
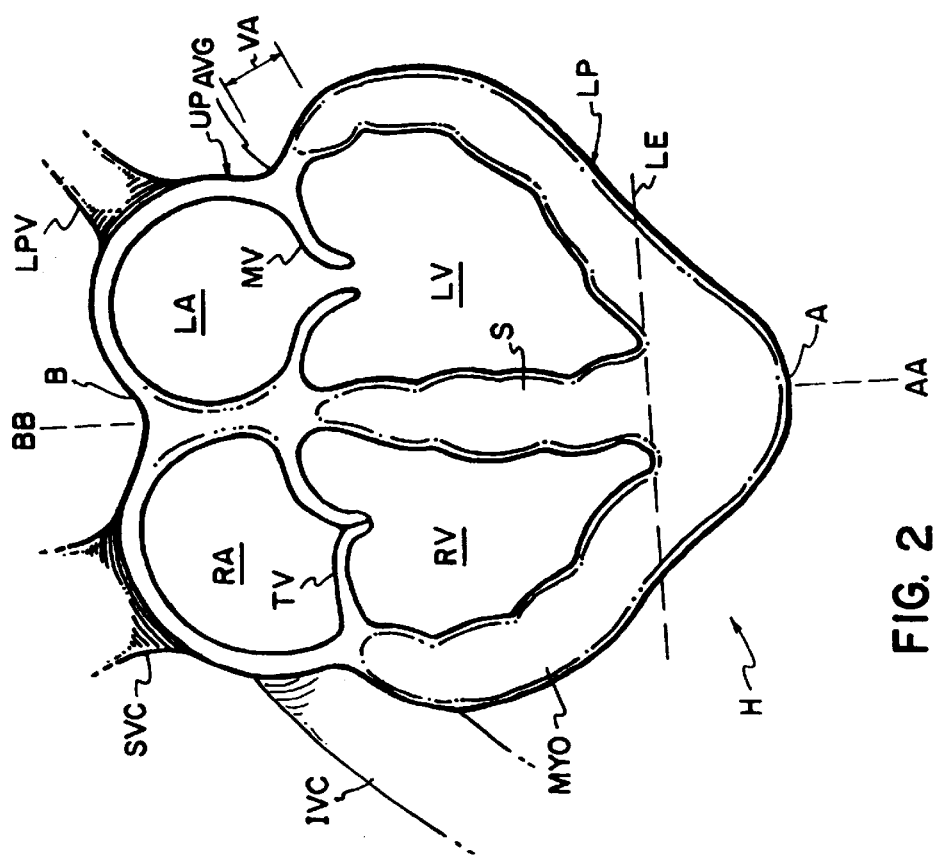
FIG. 2A is the view of FIG. 2 showing the heart during diastole.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic of cardiac insufficiency.

For ease of illustration, the progression of congestive heart disease has been illustrated and described with reference to a progressive dilation of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close. Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H.

B. Cardiac Constraint Therapy

Having described the characteristics and problems of congestive heart disease, a treatment method and apparatus e described in commonly assigned and copending U.S. patent application 09/114,757 filed Jul. 13, 1998, now U.S. Pat. No. 6,085,754. In general, a jacket is configured to surround the myocardium MYO. While the method of the present invention will be described with reference to a jacket as described in commonly assigned and copending U.S. patent application Ser. No. 09/114,57 filed Jul. 13, 1998, now U.S. Pat. No. 6,085,754, it will be appreciated the present invention is applicable to any cardiac constraint device including those shown in U.S. Pat. No. 5,800,528 and PCT International Publication No. WO 98/29401. The entire disclosure of each of these documents is incorporated herein by reference.

Figure 3A:
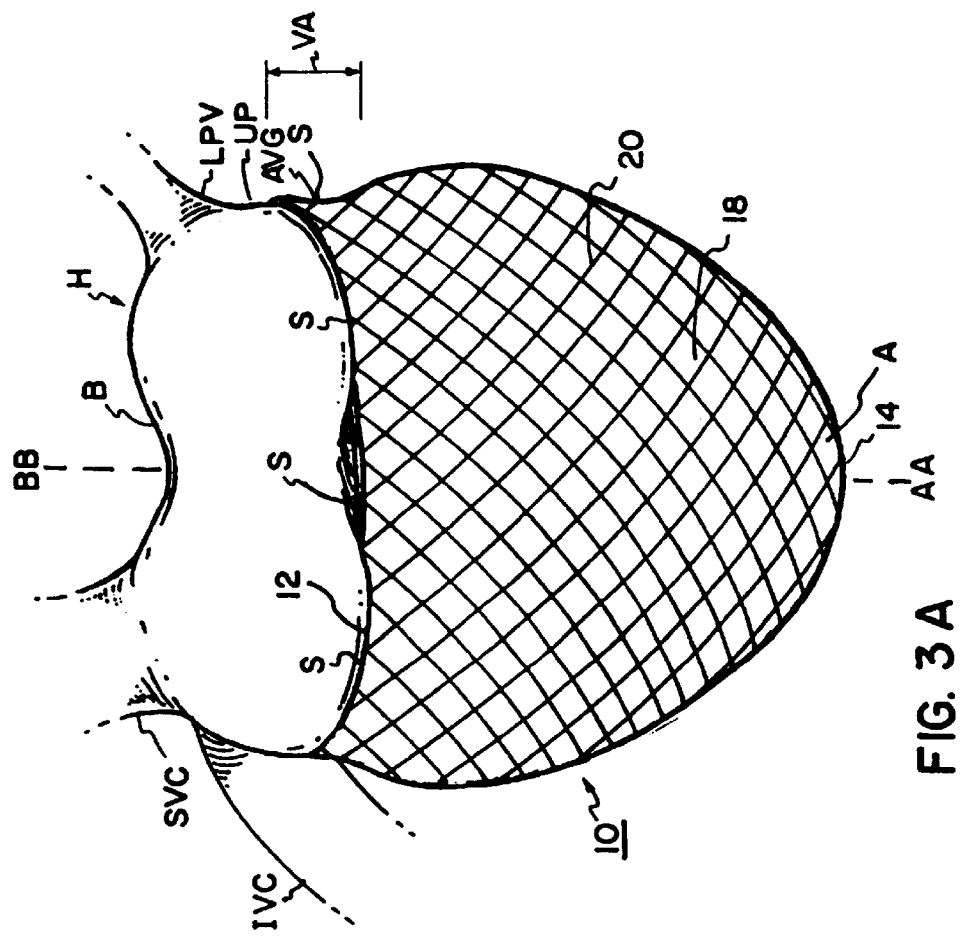
FIG. 3A is a side elevation view of a diseased heart in diastole with the device of FIG. 3 in place.
Figure 3:
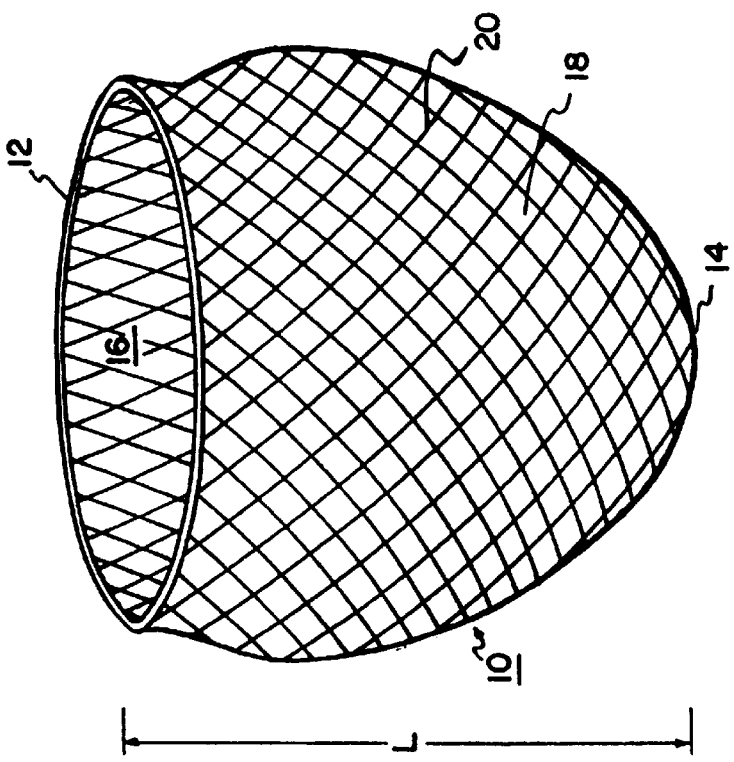
FIG. 3 is a perspective view of a cardiac constraint device.
Figure 4A:
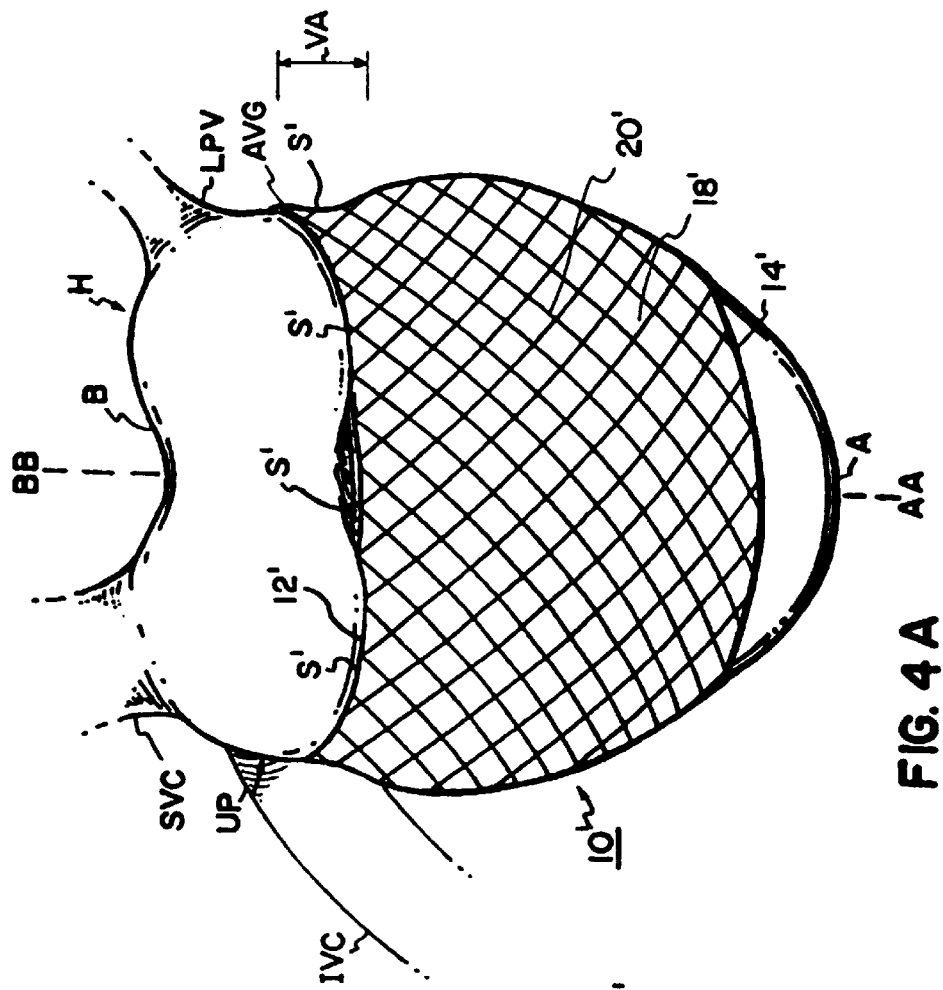
FIG. 4A is a side elevation view of a diseased heart in diastole with the device of FIG. 4 in place.
Figure 4:
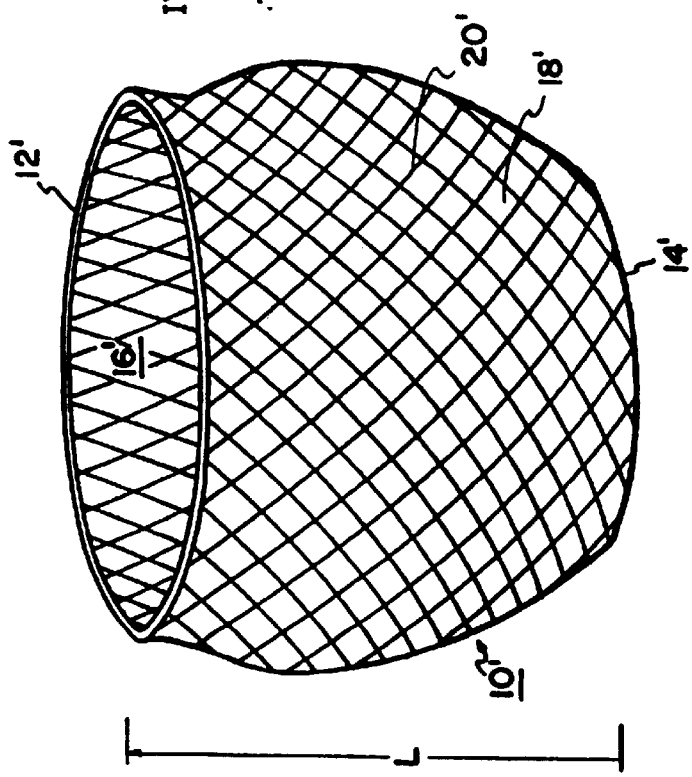
FIG. 4 is a perspective view of an alternative cardiac constraint device.

With reference now to FIGS. 3, 3A, 4 and 4A, the cardiac constraint device is shown as a jacket 10, 10' of flexible, biologically compatible material. The jacket 10, 10' is an enclosed knit material having upper and lower ends 12, 12', 14, 14'. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 preferably extends at least to A–V groove AVG and further extends to the lower portion LP to constrain at least the lower ventricular extremities LE.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

In the embodiment of FIGS. 3 and 3A, the lower end 14 is closed and the length L is sized for the apex A of the heart H to be received within the lower end 14 when the upper end 12 is placed at the A–V groove AVG. In the embodiment of FIGS. 4 and 4A, the lower end 14' is open and the length L' is sized for the apex A of the heart H to protrude beyond the lower end 14' when the upper end 12' is placed at the A–V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10' during diastole. Such placement is desirable for the jacket 10, 10' to present a constraint against dilation of the ventricular portions of the heart H.

After the jacket 10 is positioned on the heart H as described above, the jacket 10 is secured to the heart. Preferably, the jacket 10 is secured to the heart H using sutures (or other fastening means such as staples). The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

C. Tensioning of the Jacket

Figure 5:
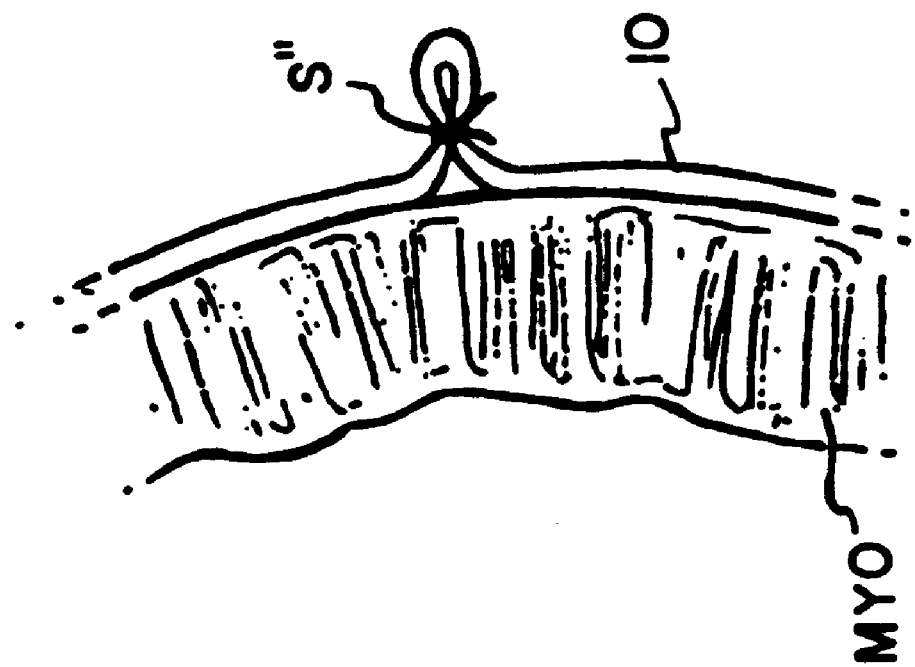
FIG. 5 is a cross-sectional view of the device of FIG. 3 overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 5) to reduce the volume 16 of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. As an alternative to gathering of FIG. 5, the jacket 10 can be provided with other arrangements for adjusting and determining the volume of the jacket. For example, as disclosed in U.S. Pat. No. 5,702,343, the jacket can be provided with a slot. The jacket can alternatively include, for example, tension indicators as disclosed in co-pending U.S. Ser. No. 09/400,018, now U.S. Pat. No. 6,174,279, or tensioning arrangements as disclosed in co-pending U.S. Ser. No. 09/400,019, now U.S. Pat. No. 6,193,648. The entire disclosure of each of these applications is hereby incorporated herein by reference.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 10 is snugly fit on the heart H but not so tight as to cause a significant increase in left ventricular pressure during diastole.

D. Delivery of the Jacket

The present invention is directed to methods and apparatuses for facilitating delivery or application of a jacket through procedures which are less invasive and less traumatic as compared to full sternotomy approaches. In general, an apparatus of the invention provides for compacting and passing a jacket through a minimally invasive opening into a patient's thorax and subsequently opening the upper end 12 of the jacket for passing over the heart. In some embodiments, the apparatus includes arrangements to facilitate securing the jacket to the heart prior to removal of the apparatus from the thorax. The apparatuses of the invention can include a biasing member which provides for collapsing and opening the upper end of the jacket through the use of components which permit selective alteration of configurational states such as hinges, shape memory materials, elastic materials, springsteel, etc.

Figure 8:
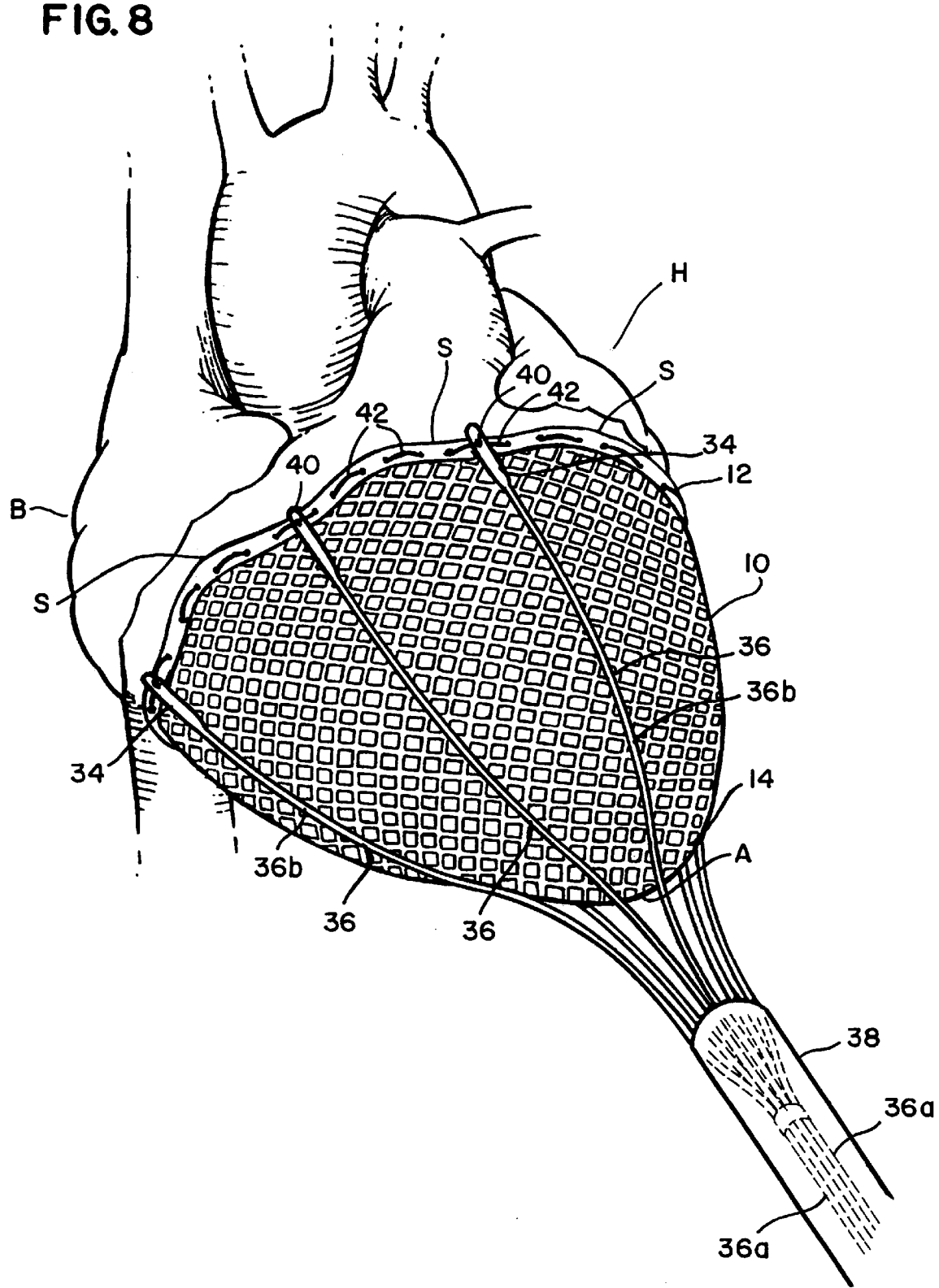
FIG. 8 is a perspective view showing a distal end of the tool of FIGS. 6 and 7 with attached jacket of FIG. 3 in use placing the jacket on a heart.

One embodiment of a delivery tool 30 is shown in FIGS. 6–8. FIGS. 6 and 7 are schematic representations of the tool 30 in longitudinal cross-section and showing only two diametrically opposed spacing arms (as will be described) and showing the tool 30 in open (FIG. 6) and closed (FIG. 7) positions (also, as will be described). FIG. 8 shows a distal end of the tool 30 with attached jacket 10 placed on a heart H.

The tool 30 includes a proximal handle 32 for hand-held manipulation by a surgeon. A plurality of attachment locations 34 are secured to the handle 32 at a distal end of the tool 30. The attachment locations 34 are preferably blunt, non-piercing and smooth, such as smooth plastic knobs, to avoid trauma to the patient as the attachment locations 34 are advanced toward the heart H as will be described.

Each of the attachment locations 34 can be individually attached to the handle 32 by a plurality of spacing arms 36. The spacing arms 36 can be strips of flexible, elongated shape memory materials having straight portions 36a and outwardly curved portions 36b. In this embodiment, the spacing arms 36 are flat, narrow sheets of spring metal having curved portions 36b configured for selective flexing toward and away from axis X—X. The proximal ends of the straight portions 36a can be secured to the handle 32. The attachment locations 34 are secured to distal ends of the curved portions 36b.

The spacing arms 36 are secured to the handle 32 for the straight portions 36a to be arranged in a closely compact cylindrical array around the longitudinal axis X—X of the tool 30. In the open position, the curved portions 36b curve outwardly from the axis X—X. Thus, the attachment locations 34 are disposed in a circular array around the axis X—X. In the embodiment of FIGS. 6–8, all spacing arms 36 are of equal length. As a result the circular array of the attachment locations 34 is in a plane perpendicular to the axis X—X. In an alternative embodiment, the lengths of the spacing arms 36 could vary. The curved portions 36b provide for attachment locations 34 to expand into an open configuration for attachment locations 34 to be spaced from axis X—X by a distance substantially greater than the spacing of the straight portions 36a from the axis X—X.

FIGS. 6 and 7 show one embodiment of a control arrangement 38 for controlling the position of the attachment locations 34. The control arrangement 38 shown here is a tube 39 which surrounds the straight portions 36a of spacing arms 36. The control arrangement 38 is axially slidable along spacing arms 36 toward and away from the distal end of the tool 30. As the tube 39 is moved distally, the tube 39 slides over the curved portions 36b urging the curved portions 36b and the connected attachment locations 34 toward axis X—X. When the tube 39 is moved proximally (i.e., the "open position"), the tube 39 is not covering the curved portions 36b. With the tube 39 in the open position, the shape memory biases the spacing arms 36 to urge the attachment locations 34 to the spaced-apart open array. When the tube 39 is moved distally to cover and compress the curved portions 36b (i.e., the "closed position"), the attachment locations 34 are urged to a compact array.

FIGS. 9 and 10 illustrate an alternative embodiment of a delivery tool 40. In this embodiment, control arrangement 39 comprises a plurality of drawstrings 50 which connect to attachment locations 51 with the free ends 52 of drawstrings 50 passing through the handle 53. The surgeon can operate the drawstrings 50 by pulling free ends 52. In the illustrated embodiment, pulling the drawstrings 50 urges the curved portions 54b of spacing arms 54 to the compact array position. Upon release of the drawstrings 50, the spacing arms 54 return to a rest position thereby moving the attachment locations 51 to the open array position. It will be appreciated that in the illustrated embodiment, the length of curved portions 54b of spacing arms 54 are not the same. The "posterior" spacing arms 54c are longer than the "anterior" spacing arms 54d. Thus, unlike delivery tool 30 of FIGS. 6 and 7, the circular array of attachment locations 51 are not in a plane perpendicular to axis X—X.

Multiple drawstrings connected to separate sets of the attachment locations 51 could be employed. For example, the attachment locations 51 could be divided into anterior and posterior sets representing anterior and posterior placement of the attachment locations around the heart. Controlled by separate drawstrings 50, the anterior 54d and posterior 54c sets could be separately manipulated by a surgeon.

The operation of a tool of the invention will now be described with reference to the tool 30 of FIGS. 6–8 and FIG. 10. However, it will be appreciated that the following discussion is applicable to all tools of the invention. Referring to FIGS. 6–8, a cardiac constraint device (such as jacket 10 in FIG. 3) can be placed within the open array of the attachment locations. In FIG. 8, the open upper end 12 of the jacket 10 is secured to the attachment locations by an attachment suture 42 passed through the material of the upper end 12 and further passed through holes 40 formed in attachment locations 34. The lower end 14 of the jacket 10 faces the handle 32. The jacket 10 is surrounded by the curved portions 36b such that the jacket open end 12 is held open sufficient to receive an apex A of the heart H when the attachment locations 34 are in the open array.

Having described the mounting of the jacket to delivery tool 30, a surgical approach using tool 30 will now be described. With reference to FIG. 11, the heart H is positioned behind the sternum ST and behind the lungs LU. The heart H rests on the diaphragm DI. Not separately shown, the heart H is surrounded by the pericardium which forms a sack around the heart H. The pericardium is attached to the diaphragm DI.

The present procedure will be described using a subxyphoid approach. However, it will be appreciated that the present invention is applicable to any procedure were a compact configuration of the jacket 10 is desired to advance the jacket 10 toward the heart H.

The lower extremity of the sternum ST is called the xyphoid XI. Below the xyphoid, surgical access can be made to the chest cavity without need for a sternotomy. After making a sub-xyphoid incision (and after any desired pre-retraction of the lower end of the lung LU), a surgeon can use the tool 30 to pass the jacket through the incision and place the jacket 10 on the heart H. The placement of the jacket can be visualized using known throscopic instrumentation and visualization procedures.

By moving the control arrangement 38 to the closed position, the distal end of the tool 30 (with attached jacket 10) can be inserted into the chest cavity through the incision and between the diaphragm DI and the lung LU. The jacket 10, curved portions 36b of spacer arms 36 and attachment locations 34 are all constrained within the compact array. The distal end of the tool 30 can now be advanced toward the apex A of the heart H through the restricted space of the chest cavity. During such advancement, the blunt attachment locations 34 avoid trauma to thoracic structures.

The pericardium may be incised to permit access of the distal end to the apex A beneath the pericardium. When the distal end of tool 30 is at the apex A, the control arrangement 38 is moved to the open position. The spacing arms 36 now urge the attachment locations 34 to the open array to open the upper end 12 of the jacket 10 sufficient to receive the apex A. With the control arrangement 38 in the open position, the distal end is passed around the apex A toward the base B of the heart H such that the jacket 10 is passed onto the heart. During such movement, the blunt attachment locations 34 can urge the pericardium away from the heart H to create a space to receive the jacket 10.

After the jacket 10 is fully placed on the heart H, sutures S are placed between the open end 12 and the heart H securing the jacket 10 in place on the heart. The attachment suture 42 is severed releasing the jacket 10 from the attachment locations 34. The tool 30 can then be withdrawn. After the attachment locations 34 have passed the apex A, the control arrangement 38 can be moved to the closed position and the tool 30 can be withdrawn from the chest cavity.

With the present invention, access to the heart is made through a restricted space requiring a less traumatic surgical approach. Further, lifting and other substantial movement of the heart H can also be reduced or avoided.

Figure 12:
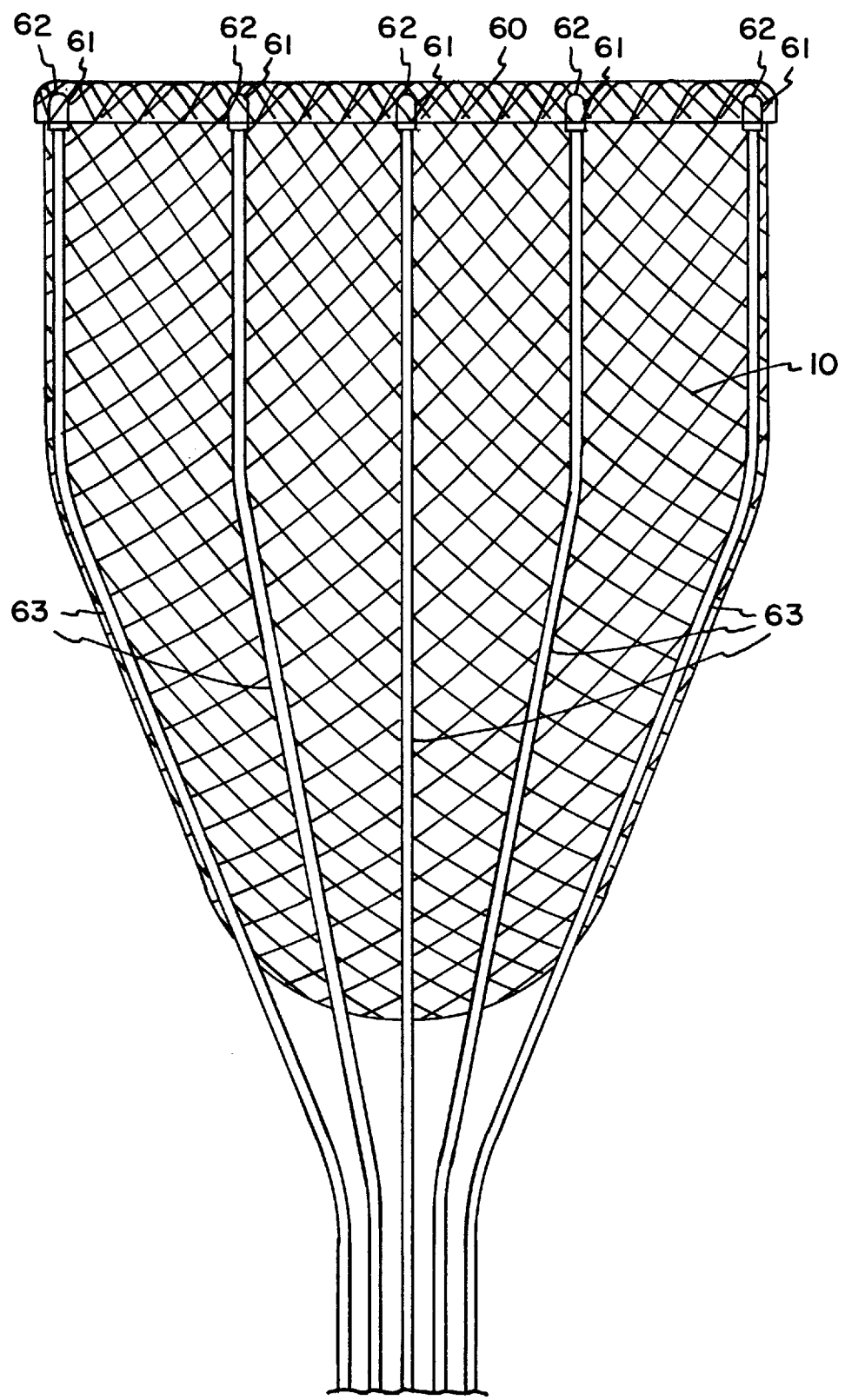
FIG. 12 is a side view of an alternative embodiment of attachment locations of a spacing arm for a delivery tool of the invention.

Referring now to FIG. 12, in an alternative embodiment, an attachment suture 42 as described above may not be used to attach jacket 10 to the spacing arms of the tool. According to this embodiment, jacket 10 includes a hem 60 having openings 61 into which can be inserted the attachment locations 62 of spacing arms 63. The previously described control arrangements and handles can be used according to this embodiment of the invention.

Alternative embodiments of the distal end of spacing arms suitable for the invention are shown in FIGS. 13–16. Each of the embodiments can be used with the tools described herein. For purposes here, elements in common with each embodiment are similarly numbered (with the addition of single, double and triple apostrophes to distinguish the embodiments).

In FIG. 13, the spacing arm 36' terminates at the distal attachment location 34' having a hole 40' to receive an attachment suture such as suture 42 in FIG. 8. The spacing arm 36' is hollow to define an internal bore 70' having a radial outlet 72' facing the axis of the delivery tool. Therefore, in use, outlet 72' faces both the upper end 12 of the jacket 10 and the heart H. A bio- or tissue-adhesive (e.g., fibrin glue) can be pumped through the bore 70' and through outlet 72' to adhere the open end 12 of jacket 10 to the heart H. Such glue can be used in conjunction with or in lieu of the sutures S of FIG. 8.

In FIGS. 14 and 15, the spacing arm 36" terminates at the distal attachment location 34" having a hole 40" to receive an attachment suture such as suture 42 in FIG. 8. The spacing arm 36" is hollow to define an internal bore 70" having a radial outlet 72" facing the axis of the delivery tool. In use, outlet 72" faces both the upper end 12 of the jacket 10 and the heart H. A coil 76" of metal or other suitable material is held in a straight configuration in the bore 70" against the natural coiling bias of the coil 76". A push rod 74" is slidably positioned in the bore 70" to push the coil 76" out of outlet 72" (as shown in FIG. 15). When pushed out of outlet 72", the coil 76" penetrates through both the open end 12 of the jacket 10 and the heart H and assumes its coiled shape thereby attaching the open end 12 of jacket 10 to the heart H. Such a coil 76" can be used in conjunction with or in lieu of the sutures S of FIG. 8.

In FIG. 16, the spacing arm 36''' terminates at the distal attachment location 34'''. The spacing arm 36''' is hollow to define an internal bore 70''' having a radial outlet 72''' facing the axis of the delivery tool. In use, outlet 72''' faces both the open end 12 of the jacket 10 and the heart H. A rod 80''' is disposed in bore 70''' with a hooked end 82''' at the outlet 72'''. Pulling on rod 80''' causes the hooked end 82''' to be pulled into the bore 70'''. The open end 12 of the jacket 10 can be placed near the outlet 72'''. The rod 80''' can then be moved back to the position of FIG. 16 with the hooked end 82''' capturing the base 12 of the jacket. Like the embodiments of FIGS. 13–15, with the embodiment of FIG. 16, the attachment suture 42 of FIG. 8 can be eliminated. The embodiment of FIG. 16 can also be used in conjunction with the embodiments of FIGS. 13–15.

From the foregoing detailed description, the invention has been described in a preferred embodiment. Modifications and equivalents of the disclosed concepts are intended to be included within the scope of the appended claims.

What is claimed is:

1. A method for applying a cardiac support device to a heart of a patient, the method comprising:
   surgically opening a chest cavity of the patient to provide access to the heart;
   providing a cardiac support device, the device comprising a jacket that defines a volume between an open upper end and a lower end;
   securing the jacket to a delivery device; the delivery device including:
   one or more attachment locations capable of releasably securing to one or more positions proximate a periphery of the open upper end of the jacket;
   a proximal handle;
   a control arrangement selectively movable between an open position and a closed position, the control arrangement connected to the one or more attachment locations such that when the control arrangement is in the closed position the one or more attachment locations are in a compact array to urge the open upper end of the jacket into a collapsed configuration and when the control arrangement is in the open position the one or more attachment locations are in an open array to urge the open upper end of the jacket into an open configuration;
   collapsing the device;
   passing the delivery device with jacket secured thereto through the opening into the chest cavity of the patient;
   opening the upper end of the jacket by moving the control arrangement into the open position; and
   passing the jacket over the heart.

2. The method according to claim 1, wherein the delivery device comprises a plurality of attachment locations.

3. The method according to claim 1, wherein the heart has a longitudinal axis from an apex to a base and an upper and lower portion divided by an A–V groove, and the step of passing the jacket over the heart comprises inserting the apex of the heart into the volume of the jacket through the open upper end.

4. The method according to claim 1, wherein the step of surgically accessing the patient's heart comprising creating a minimally invasive opening into a patient's thorax.

5. The method according to claim 1, wherein the step of surgically accessing the patient's heart comprises making a sub-xyphoid incision.

6. The method according to claim 1, further comprising a step of securing the jacket to the heart.

7. The method according to claim 6, wherein the step of securing the jacket to the heart comprises a step of suturing the jacket in place on the heart.

8. The method according to claim 6, further comprising a step of releasing the jacket from the delivery device.

9. The method according to claim 8, wherein the step of releasing the jacket from the delivery device comprises releasing the jacket from the one or more attachment locations.

10. A method for applying a cardiac support device to a heart of a patient, the method comprising:

surgically accessing the heart;

providing a cardiac support device, the device comprising
 a jacket that defines a volume between an open upper end and a lower end;
 securing the jacket to a delivery device, the delivery device comprising:
 a proximal handle;
 a plurality of spacing arms connected to the proximal handle, extending between the proximal handle and a distal end of the device, wherein the distal end of the device is configured to engage the jacket;
 a control arrangement selectively movable between an open position and a closed position, the control arrangement connected to the spacing arms such that when the control arrangement is in the closed position the spacing arms are in a compact array and when the control arrangement is in the open position the spacing arms are in an open array, where the spacing arms are open sufficient to receive an apex of a heart when the spacing arms are in the open array;

positioning the control arrangement in a closed position, wherein the spacing arms are in the compact array;

passing the delivery device with jacket secured thereto through the opening into the chest cavity of the patient; and advancing the jacket over the apex of the heart.

11. The method according to claim 10, wherein the step of surgically accessing the patient's heart comprising creating a minimally invasive opening into a patient's thorax.

12. The method according to claim 11, wherein the step of surgically accessing the patient's heart comprises making a sub-xyphoid incision.

13. The method according to claim 11, further comprising a step of securing the jacket to the heart.

14. The method according to claim 13, wherein the step of securing the jacket to the heart comprises a step of suturing the jacket in place on the heart.

15. The method according to claim 10, further comprising a step of releasing the jacket from the delivery device.

16. The method according to claim 14, further comprising a step of withdrawing the delivery device.

* * * * *

UNITED STATES PATENT AND TRADEMARK OFFICE
CERTIFICATE OF CORRECTION

PATENT NO.   : 6,579,226 B2
DATED        : June 17, 2003
INVENTOR(S)  : Vanden Hoek et al.

It is certified that error appears in the above-identified patent and that said Letters Patent is hereby corrected as shown below:

Column 5,
Line 35, "tipper" should read -- upper --

Column 6,
Line 60, "e described" should read -- are described --

Column 14,
Line 18, "claim 11" should read -- claim 10 --

Signed and Sealed this

Thirtieth Day of September, 2003

JAMES E. ROGAN
*Director of the United States Patent and Trademark Office*